United States Patent
Assell

(10) Patent No.: US 10,251,978 B2
(45) Date of Patent: *Apr. 9, 2019

(54) BONE MARROW ASPIRATE ENHANCED BONE GRAFT

(71) Applicant: Fortus Medical, Inc., Minneapolis, MN (US)

(72) Inventor: Robert Assell, St. Paul, MN (US)

(73) Assignee: Fortus Medical, Inc., Minneapolis, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/429,828

(22) Filed: Feb. 10, 2017

(65) Prior Publication Data

US 2017/0151370 A1 Jun. 1, 2017

Related U.S. Application Data

(63) Continuation of application No. 14/517,202, filed on Oct. 17, 2014, now Pat. No. 9,913,929.

(60) Provisional application No. 61/892,756, filed on Oct. 18, 2013.

(51) Int. Cl.
| | |
|---|---|
| G01N 33/567 | (2006.01) |
| A01N 63/00 | (2006.01) |
| A61L 27/36 | (2006.01) |
| A61L 27/38 | (2006.01) |
| C12N 5/00 | (2006.01) |
| C12N 5/0789 | (2010.01) |
| C12N 5/077 | (2010.01) |
| C12N 5/0775 | (2010.01) |
| A61K 35/28 | (2015.01) |
| A61K 35/32 | (2015.01) |

(52) U.S. Cl.
CPC ............ *A61L 27/365* (2013.01); *A61K 35/28* (2013.01); *A61K 35/32* (2013.01); *A61L 27/3608* (2013.01); *A61L 27/3683* (2013.01); *A61L 27/3834* (2013.01); *A61L 27/3847* (2013.01); *C12N 5/0087* (2013.01); *C12N 5/0647* (2013.01); *C12N 5/0654* (2013.01); *C12N 5/0663* (2013.01); *C12N 5/0669* (2013.01); *A61L 2430/02* (2013.01)

(58) Field of Classification Search
None
See application file for complete search history.

(56) References Cited

U.S. PATENT DOCUMENTS

| | | |
|---|---|---|
| 4,969,870 A | 11/1990 | Kramer |
| 5,269,785 A | 12/1993 | Bonutti |
| 5,456,267 A | 10/1995 | Stark |
| 5,824,084 A | 10/1998 | Muschler |
| 6,049,026 A | 4/2000 | Muschler |
| 6,132,448 A | 10/2000 | Perez |
| 6,406,454 B1 | 6/2002 | Hajianpour |
| 6,673,629 B2 | 1/2004 | Yoshimura |
| 6,723,131 B2 | 4/2004 | Muschler |
| 6,981,948 B2 | 1/2006 | Pellegrino |
| 8,137,408 B2 | 3/2012 | Kadiyala |
| 8,343,133 B2 | 1/2013 | Allee |
| 8,852,119 B2 | 10/2014 | Wawrzyniak |
| 2002/0058945 A1 | 5/2002 | Steiner |
| 2002/0161449 A1 | 10/2002 | Muschler |
| 2003/0031695 A1 | 2/2003 | Kadiyala |
| 2004/0071668 A1 | 4/2004 | Barry |
| 2005/0101963 A1* | 5/2005 | Merboth ............... A61F 2/4644 606/92 |
| 2005/0130301 A1* | 6/2005 | McKay .................. A61K 35/28 435/372 |
| 2006/0246150 A1* | 11/2006 | Thorne .............. A61K 38/1875 424/603 |
| 2007/0055282 A1 | 3/2007 | Muschler |
| 2007/0198043 A1 | 8/2007 | Cox |
| 2008/0103605 A1 | 5/2008 | Kadiyala |
| 2008/0145392 A1 | 6/2008 | Knaack |
| 2009/0081689 A1 | 3/2009 | Yamanishi |
| 2009/0137927 A1 | 5/2009 | Miller |
| 2009/0187116 A1 | 7/2009 | Noishiki |
| 2009/0287190 A1 | 11/2009 | Shippert |
| 2011/0257557 A1 | 10/2011 | Pesce |

(Continued)

FOREIGN PATENT DOCUMENTS

WO 1999/59500 A2 11/1999

OTHER PUBLICATIONS

McLain, et al. "Transpedicular aspiration of osteoprogenitor cells from the vertebral body: progenitor cell concentration affected by serial aspiration", The Spine Journal, Oct. 19, 2009, vol. 9, No. 12, pp. 995-1002.

Duguy N., et al.: "Biomaterials and osseous regeneration", Annales De Chirurgie Plastique Esthetique, Expansion Scientifique Francaise, Paris, France, vol. 45, No. 3, Jun. 1, 2000, pp. 364-376, ISSN: 0294-1260.

(Continued)

*Primary Examiner* — Julie Wu
*Assistant Examiner* — Douglas F White
(74) *Attorney, Agent, or Firm* — Michael A. Bondi; Moss & Barnett

(57) ABSTRACT

A method of preparing a bone graft. An osteoconductive matrix is placed in a receptacle. Bone marrow aspirate is provided that includes plasma, progenitor cells, hematopoietic cells, endothelial cells, red blood cells, white blood cells, platelets, bone, cartilage, thrombus or combinations thereof. The bone marrow aspirate is passed through the receptacle. At least a portion of bone marrow aspirate is retained in the receptacle. The portion of the bone marrow aspirate retained in the receptacle becomes associated with the osteoconductive matrix to form the bone graft.

9 Claims, 1 Drawing Sheet

(56) References Cited

U.S. PATENT DOCUMENTS

| | | |
|---|---|---|
| 2012/0116247 A1 | 5/2012 | Wawrzyniak |
| 2013/0030547 A1 | 1/2013 | Burkinshaw |
| 2013/0131545 A1 | 5/2013 | Azimpoor |
| 2014/0105960 A1 | 4/2014 | Zoldan |
| 2014/0257133 A1 | 9/2014 | Landrigan |
| 2015/0110890 A1 | 4/2015 | Assell |
| 2015/0164949 A1 | 6/2015 | Sowemimo-Coker |
| 2016/0325018 A1 | 11/2016 | Assell |

OTHER PUBLICATIONS

Ripamonti U., et al., "Tissue Engineering of Bone by Osteoinductive Biomaterials", MRS Bulletin, Pittsburgh, US, vol. 21, No. 11, Nov. 1, 1996, XP008005014, pp. 36-39.

Kurita, et al., "Differential Effects of Three Preparations of Human Serum on Expansion of Various Types of Human Cells", American Society of Plastic Surgeons, Dec. 20, 2007, 12 pgs.

* cited by examiner

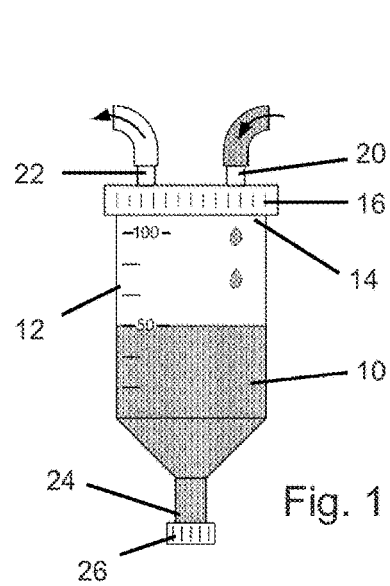
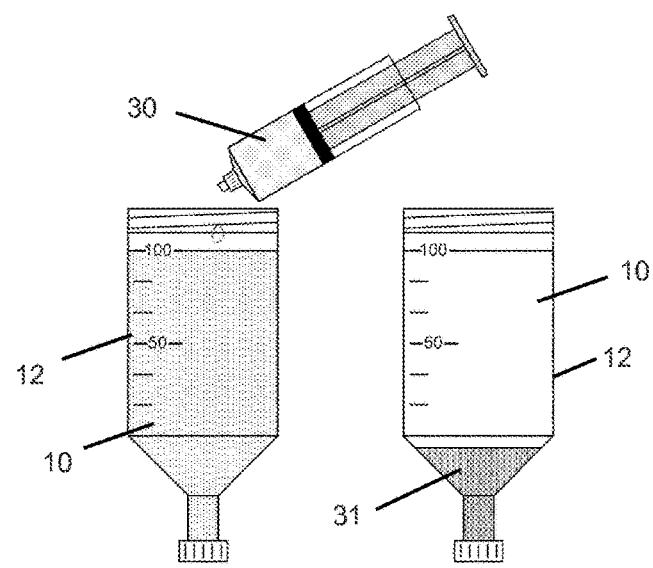
Fig. 1    Fig. 2    Fig. 3
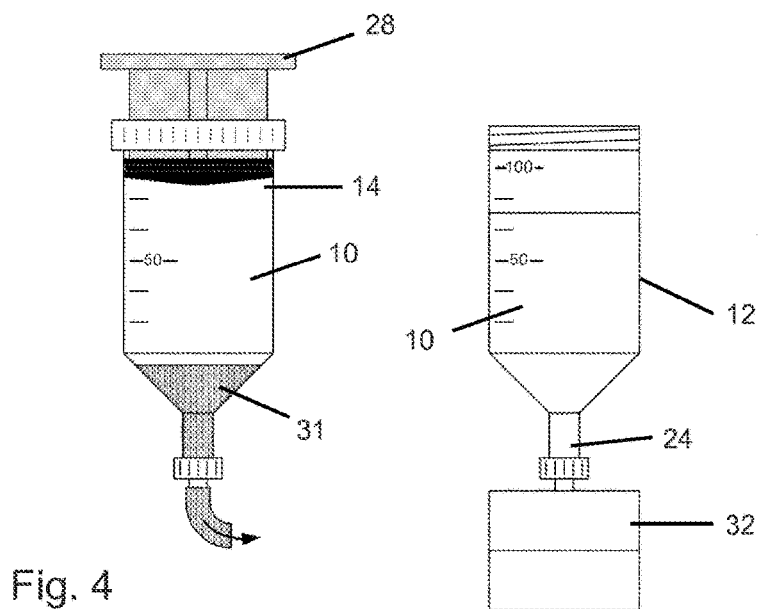
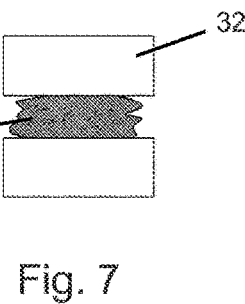
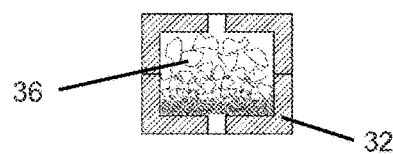
Fig. 4    Fig. 7    Fig. 5    Fig. 6

BONE MARROW ASPIRATE ENHANCED BONE GRAFT

REFERENCE TO RELATED APPLICATION

This application is a continuation of U.S. application Ser. No. 14/517,202, which was filed on Oct. 17, 2104, and this application claims priority to U.S. Provisional Application No. 61/892,756, which was filed on Oct. 18, 2013, the contents of which are incorporated herein by reference.

FIELD OF THE INVENTION

The invention relates generally to bone grafts. More particularly, the invention relates to bone marrow aspirate enhanced bone graft.

BACKGROUND OF THE INVENTION

In the US, bone grafts are most commonly used in spine fusion surgery and, more generally, in the fusion or arthrodesis of any skeletal joint. In addition, bone graft is generally used in trauma surgery for the treatment of fresh fractures and non-unions, which are typically identified as fractures within 6 months that have not healed properly. The bone graft materials typically bridge a gap between bone segments and may also provide a three-dimensional scaffold on which the bone can grow.

Bone graft treatment is also typically used in conjunction with fresh fractures where the bone has been shattered or where the patient is at a very high risk of developing a non-union fracture. Because many fractures are not this severe and can be treated with alternative methods of fixation, bone grafts are not frequently needed during fresh fracture treatments.

Two areas where bone grafts are used is in conjunction with joint reconstruction and joint revision. For example, the bone graft may be used to fill a void between the bone and joint implant in a joint reconstruction surgery.

Joint revision is much more likely to need a bone graft because a large void may result from the removal of the original implant. Joint revisions that use bone graft material therefore usually require a relatively large quantity of the bone graft material.

There are different types of bone graft materials that may be used to assist a patient's body in bone regeneration. These bone graft materials are typically classified as either natural or synthetic materials.

Natural bone graft materials are classified in the following groups. Autograft is bone graft material that is obtained from the same individual that will receive the bone graft material. Allograft is bone graft material that is obtained from another human source, which typically is from cadavers. Xeongraft is bone graft material that is obtained from another species.

Bone grafts can also be categorized by their bone-forming properties as osteoconductive, osteoinductive or osteogenic. Osteoconductivity is the ability of a material to provide an appropriate scaffold or matrix upon which new bone tissue can form. Osteoinductivity is the ability of a material to stimulate the patient's own system to form new bone. Osteogenic material generates new bone tissue itself. Osteoblasts, which can be found in bone marrow and mesenchymal cells, are the only cells that can create new bone.

Autograft bone has historically been the standard of care because of its osteoconductive, osteoinductive and osteogenic properties. At the time of surgery bone is taken from a donor site in the patient, often the iliac crest bone but others are used and then is re-implanted back into the patient at the surgical site.

Autograft is often not used, because obtaining the graft generally requires a second surgical procedure with associated risks and expenses. The autograft also typically results in significant post-operative issues, most significantly pain. An additional type of autograft, concentrated cells from bodily fluids such as blood or bone marrow, is often used as well.

In addition to autograft, many other types of bone graft are used including processed cadaver bone, i.e., allograft, in the form of demineralized bone matrix and also so called "living cell" or "stem cell" allograft. Additionally, constituents know to be involved in new bone formation, such as bone morphogenic proteins, typically produced by recombinant processing means, as used. Synthetic materials such as tri-calcium phosphate, calcium sulphate, hydroxyapatite and others are used as well.

| Summary of Bone Graft Characteristics by Material | | | |
|---|---|---|---|
| Type | Osteoconductive | Osteoinductive | Osteogenic |
| Autograft | Yes | Yes | Yes |
| Bone morphogenic proteins | No | Yes (strong) | Yes |
| Demineralized bone matrix | Yes | Minimal | No |
| Allogeneic stem cell | Yes | Unknown | Yes |
| Bone marrow aspirate | Yes | Yes (strong) | Yes |
| Synthetics | Yes | No | No |

Bone graft substitutes also fall within the classification of bone filler materials. Examples of bone graft substitutes include collagen, polymers such as silicone and some acrylics, hydroxyapatite, calcium sulfate and ceramics.

Bone cement (such as polymethylmethacylate) can be used as a bone void filler to treat bone voids or defects. For example, it can be used to repair fractured bones and vertebral bodies. The bone cement can be used either in procedures that involve direct injection of the bone cement into the fractured vertebral body (i.e., vertebroplasty) or injection of the bone cement into the vertebral body after the height of the vertebral body is restored using a pressurized balloon (i.e., kyphoplasty).

One of the disadvantages of using bone cement is that, once it is injected inside the patient, the bone cement is an inorganic material that acts as a foreign body. As such, the bone cement may not only negatively impact healing but can also lead to bone disease.

Additionally, the bone cement is typically stiffer than bone, which may increase the incidence of adjacent level fractures in the spine. Bone cement leakage may cause complications, and has been reported to occur in vetebroplasty and kyphoplasty procedures. If leakage does occur, the bone cement can cause soft tissue injury due to the high temperatures of the exothermic polymerization reaction. In addition, if the bone cement is forced into the vascular system, it can cause emboli.

Bone marrow and bone marrow aspirate concentrate is considered to have a significantly higher bioactivity than circulating blood or concentrated blood known as platelet rich plasma and is preferred for use in orthopedic applications because it contains progenitor cells and multipotent stem cells, which assist in the formation of new bone.

Traditionally, doctors have used a large bore needle to aspirate bone marrow. However, orthopedic companies have developed their own versions of bone marrow aspirate concentrate systems for use specifically with bone graft substitute. These disposable kits are used for aspirating and concentrating the stem cells found in the bone marrow onto a graft matrix to be implanted into the patient. Combined with a bone graft substitute, bone marrow aspirate concentrate may provide similar results to an autograft (Geistlich, 2011).

Bone marrow aspirate concentrate has become increasingly popular in bone growth applications, particularly spinal fusion and trauma surgery, because of its osteogenic properties. Traditionally, autograft was the gold standard grafting material in these procedures due to the presence of osteoblasts and osteogenic precursor cells, as well as its osteoconductive and osteoinductive properties.

To avoid the risks associated with autograft procurement such as donor site infection and morbidity, bone marrow aspirate concentrate has been increasingly used because it has similar properties as autograft and allows surgeons and patients to avoid autograft procurement.

Muschler, U.S. Pat. Nos. 5,824,084 and 6,049,026, are directed to a method and apparatus for preparing composite bone graft. Demineralized bone is placed in a receptacle having an inflow opening and an outflow opening. Bone marrow aspirate is introduced to the receptacle through the inflow opening.

Muschler indicates that the matrix material has a surface that selectively bonds to progenitor cells to retain the progenitor cells in the matrix. The porous nature of the matrix material allows other cells such as blood cells to pass through.

Muschler, U.S. Pat. No. 6,723,131, describes placing a biocompatible implantable matrix such as demineralized bone in a cartridge. Bone marrow aspirate is placed into a syringe that is connected to an input port on the cartridge. A collection syringe is attached to an outlet port on the cartridge to withdraw material that does not adhere to the matrix. It is indicated that the invention provides an enriched population of progenitor cells.

Merboth et al., U.S. Pat. No. 7,018,382, discloses a bone marrow mixing instrument. The instrument includes one tube for demineralized bone and one tube for bone marrow aspirate. Both of the tubes are connected to a trigger mechanism that causes the demineralized bone and the bone marrow aspirate to be discharged at the desired respective rates.

Behnam et al., U.S. Patent Publication No. 2009/0155378, describes treating bone marrow aspirate to increase osteoinductive activity. Behnam indicates that bone marrow aspirate may be mixed with osteoplant.

Rosenberg et al., U.S. Pat. No. 7,582,309, describes forming cohesive demineralized bone compositions with elongated demineralized bone fibers and a biocompatible liquid. Rosenberg indicates that the elongated demineralized bone fibers may be formed using a shaving process.

Bays et al., U.S. Pat. No. 7,776,594, discloses placing demineralized bone in a cartridge. Bone marrow aspirate is then flowed through the cartridge. A filter is placed at a distal end of the cartridge that enables air to pass therethrough but prevents any of the components in bone marrow aspirate from passing therethrough.

Huang et al., U.S. Patent Publication No. 2012/0251609, describes a demineralized cancellous bone matrix having a calcium concentration of between about 5% and 20% and where one of the dimensions of the demineralized cancellous bone matrix is between 0.5 millimeters and about 20 millimeters.

SUMMARY OF THE INVENTION

An embodiment of the invention is directed to a method of preparing a bone graft. An osteoconductive matrix is placed in a receptacle. Bone marrow aspirate is provided that includes plasma, progenitor cells, hematopoietic cells, endothelial cells, red blood cells, white blood cells, platelets, bone, cartilage, thrombus or combinations thereof. The bone marrow aspirate is passed through the receptacle. At least a portion of bone marrow aspirate is retained in the receptacle. The portion of the bone marrow aspirate retained in the receptacle becomes associated with the osteoconductive matrix to form the bone graft.

BRIEF DESCRIPTION OF THE DRAWINGS

The accompanying drawings are included to provide a further understanding of embodiments and are incorporated in and constitute a part of this specification. The drawings illustrate embodiments and together with the description serve to explain principles of embodiments. Other embodiments and many of the intended advantages of embodiments will be readily appreciated as they become better understood by reference to the following detailed description. The elements of the drawings are not necessarily to scale relative to each other. Like reference numerals designate corresponding similar parts.

FIG. 1 is a side view of collecting bone marrow aspirate in a collection vessel.

FIG. 2 is a side view showing addition of an aggregating agent to the bone marrow aspirate in the collection vessel.

FIG. 3 is a side view showing red blood cells precipitated from the bone marrow aspirate in the collection vessel.

FIG. 4 is a side view showing the precipitated red blood cells being removed from the collection vessel.

FIG. 5 is a side view showing bone marrow aspirate being passed from the collection vessel and through a graft container.

FIG. 6 is a sectional view of the graft container.

FIG. 7 is a side view showing the graft container being opened to remove the graft.

DETAILED DESCRIPTION OF THE INVENTION

An embodiment of the invention is directed to bone marrow aspirate enhanced bone graft. The bone graft thereby includes bone marrow aspirate and demineralized bone matrix.

Bone marrow aspirate contains plasma, progenitor cells, hematopoietic cells, endothelial cells, and cells derived from peripheral blood, such as red blood cells, white blood cells and platelets.

Bone marrow aspirate may be obtained from a source that minimizes the potential of immunological reactions in the person who is receiving the bone graft. As such, it is desirable for the bone marrow aspirate to be obtained from a person who is determined to be immunologically compatible with the bone graft recipient. In certain embodiments, bone marrow aspirate is obtained from the patient who will receive the graft.

Because the beneficial constituents in bone marrow aspirate represent a very small percentage of the overall volume of the bone marrow aspirate, it is desired to concentrate the bone marrow aspirate to reduce the volume of non-beneficial fractions including water and red blood cells. It is also desired to remove a significant portion of the red blood cells from the bone marrow aspirate as part of the invention because red blood cells are known to be inflammatory and, therefore, can impede the bone healing process.

The standard practice for concentrating bone marrow aspirate into bone marrow aspirate concentrate involves use of a centrifuge, which relies on density differences to separate the constituents of bone marrow aspirate. Unfortunately, red blood cells may be captured in the same density gradient as the desirable cells and constituents. Therefore, centrifugation is less than an optimal technique for separating the red blood cells from the other components of the bone marrow aspirate. Additionally, the centrifugation forces can damage the red blood cells, which could make it more difficult to separate the red blood cells from the remainder of the bone marrow aspirate.

Red blood cells carry a strong negative charge and, therefore, can be attracted to a positive charge and thereby clump together into a mass of sufficient density to precipitate out of solution.

This invention uses a reagent that utilizes the strong negative charge of the red blood cells to cause aggregation of the red blood cells. The reagent causes the red blood cells to bind together by means of electric charge attraction. Once the red blood cells have been aggregated, the aggregated red blood cells can be precipitated out of bone marrow aspirate.

The reagent having the positive charge should efficiently attract the red blood cells while facilitating separation of a large portion of the resultant product from the bone marrow aspirate.

As used herein, the term "large portion" means that more than about 90 percent by weight of the resultant product is separate from the bone marrow aspirate. In other embodiments, the term "large portion" means that more than about 95 percent by weight of the resultant product is separated from the bone marrow aspirate.

The positively charged material should also be relatively inert with respect to the other desirable components in the bone marrow aspirate such that the positively charged material does not impact the beneficial properties of the bone marrow aspirate.

Furthermore, the positively charged material should have no negative interactions if any of the positively charged material remains in the bone marrow aspirate, which then becomes incorporated into the bone graft and thereafter is implanted into the patient.

An example of one such positively charged material that may be used in conjunction with separating the red blood cells from the bone marrow aspirate is marketed under the designation PrepaCyte by BioE LLC from St. Paul, Minn. USA.

An alternative to utilizing the negatively charged characteristics to separate the red blood cells from the other portions of the bone marrow aspirate utilizes chemically reacting the red blood cells with another compound. The resulting product is more dense than the other portions of the bone marrow aspirate, which facilitates separation of the resulting product from the remainder of the bone marrow aspirate.

An example of one technique that may be used to separate the resultant product from the bone marrow aspirate is gravity separation. Because of the agglomeration of the charged or reacted components, the resultant product has sufficient size such that it settles to the bottom of the bone marrow aspirate.

In certain embodiments, the mixing of the bone marrow aspirate and the positively charged material may be done in a syringe. After the resultant product has settled in the syringe, the syringe may be oriented so that the syringe outlet is pointed upwardly and the supernatant can be discharged from the syringe.

The supernatant contains all of the desirable constituents present in bone marrow aspirate. To facilitate further processing of the supernatant for use in the bone graft material, the supernatant can be collected in another syringe.

Alternatively or additionally to utilizing the syringe, the separation can be facilitated using a centrifuge. If centrifugation is used, it should be done in a manner that minimizes disruption of the agglomerates as well as to minimize lysing of the red blood cells.

In addition to facilitating removal of red blood cells, another benefit of this reagent method is that the cells present in the supernatant are substantially unaffected and undamaged in the process of red blood cell aggregation and precipitation.

In another embodiment of the invention, the bone marrow aspirate is concentrated prior to being mixed with the demineralized bone matrix. Such separation technique should facilitate a large portion of the water in the bone marrow aspirate to be separated from the other portions of the bone marrow aspirate.

One technique that may be used in the concentration process is centrifugation. Use of a centrifuge is effective at cell concentration but is less desirable in the environment intended for this invention.

A centrifuge is a fairly large mechanical apparatus intended for laboratory use and may present challenges to be safely used in an operating room. In addition, the centrifuges are bulky thereby taking up considerable table space, noisy and relatively slow.

The intended environment for this system is the sterile operating field inside a hospital operating room at the time of surgery, i.e., at the point and time of use. Every time the centrifuge is used in the sterile field of an operating room, the centrifuge needs to be sterilized. The centrifuge needs to be accessible and useable in a manner that maintains sterility of not only the bone marrow aspirate but also the area in which the surgical procedure is being performed.

Another option for concentrating the bone marrow aspirate in a sterile environment utilizes a filter that is selected with an appropriate port size that permits water in the bone marrow aspirate to pass therethrough while preventing a significant portion of the other components in the bone marrow aspirate from passing therethrough. The filter may be a membrane type, similar to a coffee filter where a relatively thin membrane with tightly controlled porosity serves to allow passage of liquid but retention of solids larger than the pore size of the membrane.

Alternatively, the filter may consist of a bed or column of porous material such as granules or particles but may also be a porous monolithic structure such as a sponge. In the case of a filter bed or column, modulation of particle or pore size, packing density and aspect ratio of the column can be used to establish and control the effective porosity and therefore filtering specificity and efficiency. In certain cases a gradation of granule or particle size, such as from larger to smaller, can be used improve filter efficiency and specificity. A gravel and sand water filter is an example.

Trapping can occur by means of mechanical separation, i.e., cells that are too large to pass through the porous network of the filter will become lodged in the network. Alternatively the trapping can utilize adsorption to the surface of the filter components, i.e., chemical, electrical attraction, van der waals forces, covalent bonds, hydrogen bonds, electrostatic interactions, etc.

Affinity chromatography is an example of a means for trapping select constituents from a solution wherein a sorbent, such as demineralized bone matrix and certain extracellular matrix materials such as collagen, keratin sulfate, heparin, etc. are used to selectively attract and retain desirable constituents.

A suitable membrane is available under the classification of micropore. Using such a membrane causes substantially all of the components in the bone marrow aspirate to be retained on the surface of the filter medium while the water molecules pass through the filter medium.

To enhance the amount of water that is removed from the bone marrow aspirate, a reduced pressure may be utilized on the side of the filter medium that is opposite the bone marrow aspirate. The amount of the reduced pressure that is needed may be affected by factors such as the pore size of the filter medium and the desired water concentration of the concentrated bone marrow aspirate.

The membrane may be formed with a relatively large surface area as compared to a diameter of a conduit that is used to deliver the bone marrow aspirate to the filter medium. Forming the filter medium with a relatively large surface area enables the bone marrow aspirate to be dispersed in a relatively thin layer.

This relatively thin layer not only reduces the time for the water to be separate from the other portions of the bone marrow aspirate but also reduces the force that must be applied to the bone marrow aspirate during the filtration process, which reduces the potential of damage to the cells in the bone marrow aspirate.

Thereafter, the concentrated bone marrow aspirate is removed from the filter medium. An example of one suitable technique involves mechanically scraping the concentrated bone marrow aspirate. Care should be exercised to minimize not only damage to the cells in the bone marrow concentrate but also to avoid damage to the filter medium.

Another technique that may be used to remove the concentrated bone marrow aspirate from the filter medium is with a liquid such as water. The liquid may facilitate separation of the concentrated bone marrow aspirate from the filter medium with less damage than the mechanical scraping.

The volume of water used to separate the concentrated bone marrow aspirate from the filter medium should be as small as possible to achieve separation of the concentrated bone marrow aspirate from the filter medium while enabling the concentrated bone marrow aspirate to be as concentrated as possible.

In certain embodiments, the liquid may be provided from a side of the filter medium that is opposite the side of the filter medium on which the bone marrow aspirate has accumulated. In other embodiments, the liquid may be provided from the side of the filter medium on which the bone marrow aspirate has accumulated.

One challenge with forming the filter medium with a relatively large surface area as compared to a diameter of the conduit that is used to deliver the bone marrow aspirate to the filter medium is that depending on the flow rate of the bone marrow aspirate, only a portion of the filter medium may actually be used.

To enhance the efficiency of the water removal from the bone marrow concentrate, a multiple stage filter can be used. Each of the filter mediums in the multiple stage filter may have a smaller surface area than the single stage filter that is discussed above. The filter media used in the different stages may be selected with different pore size. In one such configuration, the pore size of the successive filter media has a progressively smaller pore size.

Regardless of concentration means, the desirable constituent fraction harvestable from a quantity of bone marrow aspirate taken from a patient will be a fairly small volume of material. In some embodiments, the amount of bone marrow aspirate is between about 1 $cm^3$ and about 3 $cm^3$.

In addition to the advantageous components in the bone marrow aspirate concentrate, it is desired to provide a cell binding and cell friendly, osteoconductive matrix to facilitate use of the invention in providing a strong bone graft.

The osteoconductive matrix may include a combination of demineralized bone matrix, a suitable synthetic alternative such as hydroxyapatite with the addition of other materials that fall within the classification of extracellular matrix. Examples of these materials include hyaluronic acid, collagen, keratin, elastin, fibronectin and laminin.

The osteoconductive matrix can be configured as a filter for selective retention of the desirable constituents of red blood cell depleted bone marrow aspirate supernatant whereby the osteoconductive matrix filters the desirable constituents by means of mechanical filtering such as by controlled porosity and/or by means of selective surface binding such as affinity chromatography like effect.

In certain embodiments, the combination includes greater than about 50% by weight demineralized bone matrix or synthetic substitute thereof. In other embodiments, the combination includes demineralized bone matrix or synthetic substitute thereof at a concentration of between about 60% and 90% by weight.

The demineralized bone matrix that is used in preparing the bone graft may be provided in a variety of forms such as powder, small particles or in the shape of the implant. The demineralized bone matrix can be obtained from various commercial sources such as AlloSource, Cryolife or RTI Biologics.

In certain embodiments, the demineralized bone matrix may have an average particle size of less than about 1 millimeter. In other embodiments, the demineralized bone matrix may have an average particle size of less than about 0.5 millimeters.

Because of the intended in-vivo use of the bone graft, the demineralized bone matrix should be provided in a sterile configuration to minimize the potential of introducing pathogens during the process of implanting the bone graft.

Prior to using the bone graft, the components used to fabricate the bone graft should be relatively uniformly mixed. A hollow cartridge may be used to mix the red blood cell depleted bone marrow aspirate concentrate and the filtering osteoconductive matrix, e.g., a demineralized bone/extracellular matrix composite. In certain embodiments, the cartridge may have a generally cylindrical shape with an opening that extends between opposite ends thereof.

The interior volume of the cartridge may be selected based upon the amount of bone graft that is desired to be produced. In certain embodiments, the demineralized bone matrix may substantially fill the interior of the cartridge when initially placed therein.

A cover may be provided at opposite ends of the cartridge. The covers may be removably attached to the cartridge. The attachment of the covers to the cartridge should resist the passage of water therethrough. A variety of techniques may be used to removably attach the covers to the cartridge. An example of one suitable technique for attaching the covers to the cartridge is a plurality of threads.

The covers would be attached to the cartridge during the process of mixing the bone marrow aspirate concentrate with the demineralized bone matrix. After the components are mixed, the covers may be detached from the cartridge to facilitate removing the bone graft from the cartridge.

The first cover may have an opening formed therein. The opening facilitates delivering the bone marrow aspirate concentrate to the cartridge. Proximate the opening, a connector may be provided to facilitate attaching the syringe in which the bone marrow aspirate concentrate is stored to the first cover.

The connection mechanism may be designed to be substantially water tight and facilitate transfer of the bone marrow aspirate concentrate between the syringe and the cartridge in a sterile manner. An example of one suitable connection mechanism is a leur lock. An alternative connection mechanism may be utilized a friction fit between the syringe and the cover.

The second cover may have an opening formed therein. This opening facilitates drainage of the water that passes through the cartridge. This opening may be connected to a drain line or to a drain storage container.

The filtering matrix that is placed in the cartridge can be allogeneic, synthetic or a combination thereof. The allogeneic material can be provided in a variety of forms. Examples of two such suitable forms are granules and fibers.

The allograft can be provided as mineralized or demineralized depending on the intended use of the graft. In certain embodiments, the allograft granules have a particle size that is between about 3 millimeters and about 100 microns.

Examples of the synthetic materials include calcium phosphate, tri-calcium phosphate, hydroxyapatite or combinations thereof. The synthetic materials may be provided in a variety of particle sizes such as between about 3,000 microns and 60 microns.

The bone matrix may be compacted when being placed in the cartridge to enhance the uniformity at which the bone marrow aspirate concentrate will pass through the demineralized bone matrix.

In addition to using a chromatography effect to selectively retain the efficacious components in the red blood cell depleted bone marrow aspirate in the filtering osteoconductive matrix, e.g., a demineralized bone plus extracellular matrix composite, it is also possible to use a mechanical entrapment or filtering effect to selectively retain the efficacious components in the bone marrow aspirate in the demineralized bone matrix.

The filtering matrix may have a multi-strata configuration. In certain embodiments, the filtering matrix is configured to go from high inherent porosity proximate the inlet to lower inherent porosity proximate the outlet. Alternatively, it may be possible to use a reverse descending strata configuration to help keep the smallest particles in place.

For example, a more coarsely ground demineralized bone matrix is placed proximate the entry port of the cartridge and more finely ground demineralized bone matrix is placed proximate the outlet port of the cartridge. It is also possible to put one or more additional layers between the more coarsely ground layer and the more finely ground layer that progressively include more finely ground particles.

The bone matrix may consist of a thin layer of 250+ micron particles that is placed on the membrane. Next, a slightly thicker layer of 100+ micron particles is placed in the cartridge. This process is repeated with 250+ micron particles, 500+ micron particles, 1,000+ micron particles and 3,000+ micron particles.

The effective porosity of a bed of granules is between about 25 percent and about 30 percent of the granule size. For example, a bed of 100 micron granules will exhibit an effective porosity of about 25 microns to about 30 microns. The typical granule size range of sieved particles can be less than 40 microns, between 60 microns and 100 microns, between 100 microns and 250 microns, between 250 microns and 500 microns, between 500 microns and 1,000 microns, between 1,000 microns and 3,000 microns and greater than 3,000 microns.

The bone marrow aspirate or supernatant will be introduced at the top of the cartridge and then pass through the 3,000 micron layer and then the 1,000 micron layer and so on. The larger constituents that may be in the bone marrow aspirate such as small pieces of bone, cartilage or thrombus will be trapped in the first layer but the smaller constituents will pass through all the way down to the stem cell size, which will be trapped in the 60 micron layer or the 100 micron layers as the size of these cells is in the range of 15 to 50 microns.

A filter membrane can be provided proximate the outlet port of the cartridge that retains the bone matrix in the cartridge. In certain embodiments, the membrane has a particle size of about 250 microns. The membrane will retain the particles having a size of greater than 250 microns. The 250 micron layer will retain the 100 micron particles. The 100 micron layer will retain the 60 micron particles.

It is also possible to utilize an affinity mechanism to trap desirable cells in the bone matrix. This process may be a preferred retention mechanism as in certain configurations, it is more discriminating for the preferred cells rather than just size. A person of skill in the art will appreciate that a variety of compositions may be utilized based upon the cells that are desired to be trapped in the bone matrix. For example, the attractant composition may exhibit a charge that causes the desired cells to be attracted to the bone matrix.

This attractant composition can be mixed with the bone matrix before the bone matrix is placed into the cartridge. Alternatively, attractant composition can be passed through the bone matrix after the bone matrix is placed in the cartridge.

The second syringe having the bone marrow aspirate concentrate placed therein is connected to the inlet port on the cartridge. A force is then applied to the second syringe to cause the bone marrow aspirate concentrate to move from the second syringe to the cartridge.

To minimize the potential of a channel being formed through the demineralized bone matrix in the cartridge, the rate at which the bone marrow aspirate concentrate is ejected from the second syringe should not be too fast.

Another factor believed to play an important role in distribution of the bone marrow aspirate concentrate throughout the demineralized bone matrix is the use of a relatively consistent pressure to cause the bone marrow aspirate concentrate to be ejected from the second syringe.

The force to cause the bone marrow aspirate concentrate to be ejected from the second syringe may be applied by a person's hand or hands. If the force is applied by the person's hand or hands, guidance should be provided regarding the total time for all of the bone marrow aspirate concentrate to be ejected from the second syringe.

Alternatively, the second syringe may be placed in a mechanical ejector that is capable of ejecting the bone marrow aspirate concentrate from the second syringe at approximately the desired rate. In one such configuration, the mechanical ejector is a spring. In other embodiments, the ejector is operated with hydraulic pressure, pneumatic pressure and/or pressure applied by a motor.

Proximate a second end of the cartridge that is opposite the end of the cartridge to which the second syringe is attached, a filter membrane may be placed. The filter membrane may be formed with a pore size that is sufficiently small such that it resists passage of the demineralized bone matrix and all of the components in the bone marrow aspirate concentrate except water. The filter membrane may also permit air and other gases that are present in the demineralized bone matrix and/or the bone marrow aspirate concentrate to pass therethrough.

Allowing the water to pass through the filter membrane facilitates further concentration of the bone marrow aspirate concentrate during the process of intermixing the bone marrow aspirate concentrate and the demineralized bone matrix.

The size and/or number of pores in the filter membrane can also be used to control the amount of water that passes through the filter membrane and, as such, can adjust the moisture level of the bone paste that is prepared from the intermixing of the bone marrow aspirate concentrate and the demineralized bone matrix.

While it is possible to attach a separate filter to the second end of the cartridge, such a configuration would enable a portion of the bone marrow aspirate concentrate and the demineralized bone to exit from the second end of the cartridge. Since the opening in the second end of the cartridge has a diameter that is considerably smaller than the diameter of the cartridge, the bone marrow aspirate concentrate and the demineralized bone matrix may preclude the flow of water out of the second end of the cartridge. Accordingly, it may be desirable to prevent the bone marrow aspirate concentrate and the demineralized bone matrix from exiting the second end of the cartridge.

A person of skill in the art can appreciate that a variety of porous materials can be used to prevent the bone marrow aspirate concentrate and the demineralized bone matrix from exiting the second end of the cartridge. An example of one such porous material is filter media having a pore size that is smaller than the pore size of the components of the bone marrow aspirate concentrate and the demineralized bone matrix.

After all of bone marrow aspirate concentrate has been ejected from the second syringe into the cartridge, the bone marrow aspirate concentrate and the demineralized bone matrix may be sufficiently well mixed such that the resulting bone paste is ready for use. In other situations, additional mixing may be desired to ensure that the bone paste is relatively uniformly mixed.

One option for applying the bone paste is to remove at least one of the covers from the cartridge and then scoop or otherwise remove the bone paste from the cartridge. In another configuration, the first cover is removed and replaced with a plunger mechanism and the second cover is removed and replaced with a dispensing tip. This process thereby converts the cartridge into a syringe such that the plunger can be used to dispense the bone paste from the cartridge in a controlled manner.

Depending on the desired application of the bone paste, the bone paste can be formed with different flowabilities. The flowability of the bone paste can be adjusted by changing the amount of water in the bone marrow aspirate concentrate as well as the amount of water that is allowed to pass through the filter membrane at the second end of the cartridge.

Alternatively to applying the bone graft as a paste, it is possible to form the bone graft material into the desired shape of the implant. After the bone graft material is formed into the desired shape, the moisture content of the bone graft material can be reduced to cause the implant to become more rigid. An example of one technique that may be used to reduce the moisture content of the implant is heating.

The physical properties of the bone graft material may be enhanced by the addition of at least one additive to the bone graft material. An example of one additive is collagen.

In another embodiment of the invention, the demineralized bone matrix is formed with a larger particle size. The bone marrow aspirate concentrate may flow through the cartridge more than one time to provide the components in the bone marrow aspirate concentrate with a greater opportunity to associate with the demineralized bone matrix particles.

The product and method of the present invention are described in the following examples. These examples are provided as an illustration of the invention and are not intended to limit the invention.

Example

As an initial aspect in performing the method of this invention, bone marrow is obtained from a person. A person of skill in the art will appreciated that a variety of techniques may be used to obtain the bone marrow. As noted above, it may be possible for the bone marrow to be obtained from the same person on which it is intended to use the bone graft prepared therefrom. In other situations, the bone marrow is obtained from a person who is immunologically compatible with the person in which it is intended to use the bone graft prepared therefrom.

The bone marrow aspirate 10 is placed in a collection vessel 12 that having a generally cylindrical shape, as illustrated in FIG. 1. A first opening 14 is provided proximate an upper end of the collection vessel 12. It may be possible to attach a first cover 16 the first opening 14. The first cover 16 includes an inlet port 20 and an outlet port 22. The first cover 16 may be removably attached to the collection vessel 12 such as using complementarily shaped threads on the collection vessel 12 and the first cover 16.

A second opening 24 is provided proximate a lower end of the collection vessel 12. The second opening 24 may have a size that is smaller than the first opening 14. Forming the second opening 24 with a smaller size enhances the ability to separate the precipitated red blood cells from the bone marrow aspirate while minimizing the loss of the other portions of the bone marrow aspirate, which is described in more detail herein.

In certain embodiments, a size of the second opening 24 is less than about 25 percent of a size of the first opening 14. In other embodiments, the side of the second opening 24 is less than about 10 percent of the size of the first opening 14.

A second cover 26 is attached to the second opening 24 to thereby control the discharge of product from the second opening 24. In certain embodiments, the second cover 26 is removably attached to the collection vessel 12 such as using complementary shaped threads on the collection vessel 12 and the second cover 26. While not illustrated, the second cover 26 may comprise a valve that allows the flow of material from the collection vessel 12 to be controlled.

The aggregating agent 30 is then added to the collection vessel 12, as illustrated in FIG. 2. The aggregating agent 30 causes red blood cells in the bone marrow aspirate to agglomerate and then precipitate from bone marrow aspirate, as illustrated at 31 in FIG. 3. The aggregation and settling was substantially complete over a period of time of about 25 minutes. Such precipitation facilitates separation of the red blood cells from the other portions of the bone marrow aspirate.

Next, the precipitated red blood cells are separated from the other portions of the bone marrow aspirate. In certain embodiments, the first cover 16 is detached from the collection vessel 12 and a plunger 28 is attached to the collection vessel 12 proximate the first opening 14. The plunger 28 urges the precipitated red blood cells from the collection vessel 12 through the second opening 24. The precipitated red blood cells that are urged from the collection vessel 12 may be discarded. This process was done slowly to minimize loss of the bone marrow aspirate other than the red blood cells.

A graft filter chamber 32 is attached to the second opening 24, as illustrated in FIG. 5. The graft filter chamber 32 has an opening 34 formed therein, as illustrated in FIG. 6. The opening 34 is filled with bone graft material 36. In certain embodiments, the bone graft material 36 is provided in at least two granulations. More coarsely ground bone graft material 36 is placed proximate a proximal end of the graft filter chamber 32 and more finely ground bone graft material 36 is positioned proximate a distal end of the graft filter chamber 32, as illustrated in FIG. 6. The graft filter chamber 32 may include at least two sections that are detachable from each other after the process is completed to remove the graft therefrom.

Suction was applied to the distal end of the graft filter chamber 32 to cause the bone marrow aspirate to be drawn through the bone graft material 36. Alternatively or additionally, the bone marrow aspirate may be urged through the graft filter chamber 32 such as using a plunger similar to illustrated in FIG. 4. The bone graft material 36 acts as a filter to cause beneficial components in the bone marrow aspirate to be retained in the graft filter chamber 32.

The graft filter chamber 32 is opened as illustrated in FIG. 7 to access the bone graft material 36. In certain embodiments, the bone graft material may be used upon formation. In other embodiments, the bone graft material is stored prior to use. A person of skill in the art will appreciate the storage conditions for the bone graft material to maintain the efficacy of the bone graft material.

It is to be understood that other embodiments may be utilized and structural or logical changes may be made without departing from the scope of the present invention. The preceding detailed description, therefore, is not to be taken in a limiting sense, and the scope of the present invention is defined by the appended claims.

It is contemplated that features disclosed in this application, as well as those described in the above applications incorporated by reference, can be mixed and matched to suit particular circumstances. Various other modifications and changes will be apparent to those of ordinary skill.

The invention claimed is:

1. A method of preparing a bone graft comprising:
    placing an osteoconductive matrix in a receptacle,
    providing bone marrow aspirate comprising plasma, progenitor cells, hematopoietic cells, endothelial cells, red blood cells, white blood cells, platelets, bone, cartilage, thrombus or combinations thereof;
    mixing the bone marrow aspirate with an effective amount of a binding reagent that is capable of binding with red blood cells in the bone marrow aspirate to form bound red blood cells;
    aggregating the bound red blood cells;
    separating the aggregated bound red blood cells from the bone marrow aspirate to provide a red blood cell depleted bone marrow aspirate without the use of a centrifuge, wherein greater than 90 percent by weight of the red blood cells are removed from the red blood cell depleted bone marrow aspirate;
    passing the red blood cell depleted bone marrow aspirate through the receptacle; and
    retaining at least a portion of the red blood cell depleted bone marrow aspirate in the receptacle, wherein the portion of the red blood cell depleted bone marrow aspirate retained in the receptacle becomes associated with the osteoconductive matrix to form the bone graft.

2. The method of claim 1, wherein an affinity mechanism between the osteoconductive matrix and the bone marrow aspirate causes the portion of the red blood cell depleted bone marrow aspirate to be retained in the receptacle.

3. The method of claim 1, wherein mechanical entrapment causes the portion of the red blood cell depleted bone marrow aspirate to be retained in the receptacle.

4. The method of claim 1, and further comprising concentrating the red blood cell depleted bone marrow aspirate before passing the red blood cell depleted bone marrow aspirate through the receptacle.

5. The method of claim 1, wherein the osteoconductive matrix is placed in the receptacle in a multi-strata configuration in which the osteoconductive matrix has different particle size regions.

6. The method of claim 1, and further comprising placing a membrane in the receptacle to substantially retain the osteoconductive matrix in the receptacle as the red blood cell depleted bone marrow aspirate is passed through the receptacle.

7. The method of claim 1, wherein a substantially constant pressure is used to urge the red blood cell depleted bone marrow aspirate through the osteoconductive matrix to substantially uniformly distribute the red blood cell depleted bone marrow aspirate in the osteoconductive matrix.

8. The method of claim 1, and further comprising controlling flow of water from the outlet port to provide the bone graft with a viscosity that is within a selected range.

9. The method of claim 1, wherein the osteoconductive matrix comprises a demineralized bone matrix, hydroxyapatite, hyaluronic acid, collagen, keratin, elastin, fibronectin, laminin or combination thereof.

* * * * *